United States Patent
Diaz Garcia et al.

(10) Patent No.: US 9,540,416 B2
(45) Date of Patent: Jan. 10, 2017

(54) PURIFICATION PROCESS

(71) Applicants: Juan Jose Diaz Garcia, Hamilton, MT (US); Margit Holzer, Dveommartemont (FR)

(72) Inventors: Juan Jose Diaz Garcia, Hamilton, MT (US); Margit Holzer, Dveommartemont (FR)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 225 days.

(21) Appl. No.: 13/828,852

(22) Filed: Mar. 14, 2013

(65) Prior Publication Data
US 2014/0030318 A1    Jan. 30, 2014

(30) Foreign Application Priority Data
Jul. 27, 2012  (GB) .................................. 1213364.1

(51) Int. Cl.
*A61K 36/00*     (2006.01)
*C07J 71/00*     (2006.01)
*C07H 1/08*      (2006.01)
*C07H 15/256*    (2006.01)

(52) U.S. Cl.
CPC ............. *C07J 71/0052* (2013.01); *C07H 1/08* (2013.01); *C07H 15/256* (2013.01); *A61K 2236/00* (2013.01)

(58) Field of Classification Search
None
See application file for complete search history.

(56) References Cited

U.S. PATENT DOCUMENTS

| 5,057,540 A | 10/1991 | Kensil et al. |
| 6,524,584 B2 * | 2/2003 | Kensil .................... 424/184.1 |
| 2002/0044940 A1 * | 4/2002 | Kensil ............... A61K 39/39 424/184.1 |

FOREIGN PATENT DOCUMENTS

| CN | 102232977 | 11/2011 |
| CN | 102351938 | 2/2012 |
| CN | 102462718 | 5/2012 |
| GB | 2373743 A | * 10/2002 |
| WO | 9953933 | 10/1999 |
| WO | 2007068907 | 6/2007 |

OTHER PUBLICATIONS

Pham et al, Saponins from Quillaja saponaria Molina: isolation, characterization and ability to form immuno stimulatory complexes (ISCOMs). Current drug delivery, (Oct. 2006) vol. 3, No. 4, pp. 389-97.*
Ganzera et al, Separation of the major triterpenoid saponins in Bacopa monnieri by high-performance liquid chromatography. Analytica Chimica Acta (2004), 516(1-2), 149-154.*
Ganzera, et al., "Separation of the major triterpenoid saponins in Bacopa monnieri by high-performance liquid chromatography" Analytica Chimica Acta; 2004; pp. 149-154; vol. 516(1-2).
Pham, et al., "Saponins from Quillaja saponaria Molina: Isolation, Characterization and Ability to Form Immuno Stimulatory Complexes (ISCOMs)" Current Drug Delivery; 2006; pp. 389-397; vol. 3.
Higuchi, et al., "An acylated Triterpenoid Saponin From Quillaja Saponaria" Phytochemistry; 1988; pp. 1165-1168.
Kensil, et al., "Separation and Characterization of Saponins with Adjuvant Activity from Quillaja saponaria Molina Cortex." The Journal of Immunology; 1991; pp. 431-437; vol. 146.
Li, "The current state of extracting and separating natural steroidal saponin." Liaoning Chemical Industry; 2010; pp. 128-430 and 443; vol. 39(4).
Deng, et al., "Separation and Purification of Ophiopogonin D." Journal of Dalian Institute of Light Industry; 2011; pp. 235-237; vol. 30 (4).

* cited by examiner

*Primary Examiner* — Qiuwen Mi
(74) *Attorney, Agent, or Firm* — Joseph Schuller; Rebecca Stephens

(57) ABSTRACT

The present disclosure concerns methods for producing purified saponins, such as QS-21, which reduces the number of necessary lyophilization cycles to one by a step of solvent exchange and optional subsequent exposure of the purified saponin product to at least one exposure to dry gas followed by exposure to a vacuum to further rid the purified saponin product of residual solvent molecules.

29 Claims, No Drawings

PURIFICATION PROCESS

RELATED APPLICATIONS

The present application claims priority to United Kingdom Patent Application No. 1213364.1 filed on 27 Jul. 2012, pursuant to 35 USC §111a, the contents of which are incorporated herein.

FIELD OF THE INVENTION

This disclosure relates to the purification of biological products. More specifically, this disclosure concerns the purification of saponins useful as adjuvants.

BACKGROUND TO THE INVENTION

Saponins, steroid or triterpenoid glycosides found widely in the plant kingdom, have a wide range of medicinal and commercial uses. The saponins of some plant species have been shown to be useful as adjuvants that can be used to enhance immune responses to specific antigens. Some types of plant saponin adjuvants not only enhance immune responses to antigens but can also preferentially induce specific types of cell mediated immune responses.

Current procedures for purifying pharmacologically useful saponins are not optimal in terms of product uniformity, reconstitutability, or homogeneity. In addition, current methods of purifying saponins can take as long as 14 days.

In view of the potential usefulness of immunogenic compositions containing saponins, a need exists for more efficient saponin purification methods.

SUMMARY OF THE INVENTION

The present disclosure relates to a method of purifying saponins from solutions comprising solvents. The method involves performing a solvent exchange on a solution comprising at least one saponin in a solvent further comprising a solubilizing component to reduce the amount of solubilizing components in the solution. Following solvent exchange, the replaced solvent is removed to yield a dried saponin product. In an optional subsequent step, several exposures of the dried saponin product to a dry gas followed by vacuum cycles are used to remove any solvent molecules that remain within the dried saponin product.

The present invention further claims a purified *Quillaja saponaria* Molina saponin QS-21. QS-21 saponin product produced by this process which is more homogenous than that produced over current methods. The present invention further relates to the use of the highly purified QS-21 product produced by the method disclosed herein as immune adjuvants in vaccines.

DETAILED DESCRIPTION OF THE INVENTION

Introduction

The present disclosure concerns methods for producing purified saponins, such as QS-21. The procedure disclosed herein reduces the number of necessary lyophilization cycles to one by a step of solvent exchange and optional subsequent exposure of the purified saponin product to at least one exposure to dry gas followed by exposure to a vacuum to further rid the purified saponin product of residual solvent molecules.

Purified saponins are used medicinally, industrially, and in food and beverage products. Some saponins, such as those extracted from the bark of the South American tree *Quillaja saponaria* Molina (Quillaja saponins), for example, QS-21, have pharmacological value as immunological adjuvants because they exhibit low toxicity while inducing strong Th1 and Th2-type immune responses when co-administered with an antigen. Additionally, such saponins have been shown to elicit moderate cytotoxic T lymphocytes responses to some proteins.

To be safely used, saponins must be separated from other plant derived material, including, in the case of Quillaja saponins, other more toxic saponins. Although methods exist for purifying saponins, current purification methods can take up to 14 days. Saponins produced by current methods can be non-homogenous.

Saponin purification by the disclosed methods provides several significant benefits over current methods. Specifically, the method disclosed herein offer the benefit that it can reduce the time required for large-scale saponin purification methods by almost half over current methods. Current methods can take as long as 14 days while the total purification time by the present method can be only 6 days. Moreover, saponins purified by the method disclosed herein retain no more solvent or water than purified saponin products obtained using current procedures, typically involving multiple lyophilization steps which can take twice as long. Water in the final product contributes to product degradation in purified saponin compositions. Furthermore, solvent components, such as organic molecules, usually must be reduced significantly from dried saponin products for their safe pharmacological use.

The method disclosed herein is further beneficial over current methods because, by obviating the need for a second lyophilization, it produces a more homogeneous dried saponin product than current methods requiring two lyophilization steps.

Thus, one aspect of this disclosure relates to a method for producing highly purified saponin compositions. The method disclosed herein results in the production of a highly homogeneous purified saponin product with little to no residual water or solvent molecules. The disclosure herein provides a method for purifying at least one saponin in a solution by providing at least one saponin in a first solvent including a solubilizing component; replacing at least a portion of the solubilizing component with an exchange solvent, thereby producing a replaced solvent; removing the replaced solvent, to produce a dried saponin product including at least one saponin; and optionally contacting the dried saponin product with a dry gas such that any solvent molecules remaining in the dried saponin product disperse into the gas, thereby producing a gas-cleansed dried saponin product. In the context of purification of saponins, purification includes providing a solution comprising at least one saponin and replacing at least a portion of the solubilizing component with an exchange solvent. Optionally, prior to purification from solution, saponins can be isolated from other solution components (e.g., plant material, organism tissue, undesired chemicals and molecules as well as other debris) by various chemical or chromatographic methods.

The solubilizing component can include at least one of the following: water, an organic molecule, an alcohol, an acid or a base. Alternatively, the solubilizing component can be any molecule that will completely or partially disperses the at least one saponin into the solvent. In some embodiment, the solubilizing component can include an organic molecule. For example, the solubilizing component can include acetonitrile.

Optionally, the saponin in a first solvent can be partially purified by column chromatography. For instance, the saponin in a first solvent can be provided in the form of HPLC column elate or phenyl chromatography column eluate. For example, the saponin in a first solvent can be provided in the form of C8 HPLC column elate. Typically, C8 HPLC column eluate used for saponin purification includes at least about 22% acetonitrile vol/vol. Thus, the saponin in a solvent can include at least about 22%. For instance, the saponin in a first solvent can include at least about 50% acetonitrile. As well, the saponin in a first solvent can include between about 30% and 65% volume/volume acetonitrile. For example, between about 40% and 62% volume/volume acetonitrile is a suitable range. For instance, the saponin in a solvent can include about between about 58% and 62% volume/volume acetonitrile. The term about is included in the above stated acetonitrile concentrations to indicates that the given value is approximate and may vary by plus or minus 5%.

Following obtaining a solution of saponins in a solvent, solvent replacement can be performed. The replacement of at least a portion of the solubilizing component can be done by exchanging either an identical or a non-identical volume of the first solvent with an exchange solvent. Solvent replacement can be achieved by any one of diafiltration, ultrafiltration or dialysis. Typically, the replaced solvent will contain at least 15% vol/vol acetonitrile but no more than 22% vol/vol acetonitrile.

Optionally, the replacement of at least a portion of the solubilizing component can be performed in a system including a semi-permeable containment vessel that is selectively permeable such that at least one solvent component will pass through the permeable portion of the vessel and at least one saponin will be retained when at least one saponin and a first solvent is introduced to the semi-permeable containment vessel. For example, the semi-permeable containment vessel used can include a single semi-permeable membrane and solvent replacement can be achieved by immersing the semi-permeable containment vessel comprising the at least one saponin and a first solvent in an exchange solvent and allowing the solvents separated by the membrane to reach equilibrium by diffusion.

Alternatively, the semi-permeable containment vessel can include a channel permeable to the solution including the at least one saponin in a solvent that is surrounded by at least one semi-permeable structure. In this embodiment, the at least one saponin and a first solvent can be moved through the channel of the containment vessel at a positive pressure relative to the outside of the vessel by way of hydrostatic pressure such that at least one component of the solution is forced across the semi-permeable portion of the containment vessel to the outside (e.g., any portion of the semi-permeable structure not in contact with the channel) and at least one molecule of the solution travels the entire length of the channel. In this embodiment, at least a portion of the solubilizing component can be replaced with an exchange solvent by adding the exchange solvent to the inside (e.g., the channel) of the containment vessel.

In another embodiment, the semi-permeable containment vessel can include a non-permeable container including a first compartment and a second compartment separated by a semi-permeable membrane. In this embodiment, the at least one saponin and a first solvent can be placed into the first compartment of the containment vessel which can then be made a positive pressure relative to the second compartment such that at least one component of the solution can be forced across the semi-permeable portion of the containment vessel and at least a portion of the solubilizing component can be replaced with an exchange solvent by addition of the exchange solvent to the first compartment of the vessel.

Following solvent replacement, the replaced solvent can be removed from the saponin product to yield a dried saponin product. Removal of the replaced solvent can be performed by any one or more of the following processes: lyophilization, heat exposure or rotary evaporation. In a particular embodiment, lyophilization is used to remove the replaced solvent. An exemplary lyophilization procedure is provided in the Examples section. However, lyophilization can be performed by essentially any methods known in the art. Optionally, lyophilization can be performed in Gore brand disposable LYOGUARD™ trays. Optionally, more than one removal step can be performed, e.g., if further drying of the sample is desired.

Optionally, following solvent removal, the dried saponin product can be further rid of any remaining solvent molecules by contacting the dried saponin product with a dry gas to produce a gas-cleansed dried saponin product. Optionally, the dried saponin product can be contacted by a dry gas in a vacuum. In some embodiments, the contacting the dried saponin product with a dry gas is done at greater than 700 µbar of pressure. For instance, the dried saponin product can be contacted with dry gas at 800 µbar of pressure. Optionally, the dried saponin product can be kept in contact with the dry gas for at least 1 minute. For instance, the dried saponin product can be kept in contact with the dry gas for 5 minutes or longer.

Optionally, following the contacting the dried saponin product with a dry gas the dry gas is removed. For example, such removal can be effected by vacuum pressure. In some embodiments, the dry gas is removed by vacuum pressure of less than 100 µbar. For instance, the dry gas can be removed by a vacuum pressure of 50 µbar. Optionally, the vacuum pressure can be applied for greater than 1 minute. For example, the vacuum pressure can be applied for 30 min.

Optionally, following removal of the dry gas by vacuum pressure, one or more of the preceding steps of contacting the dried saponin product with a dry gas can be repeated. Optionally, the pressure of the vacuum can be raised to atmospheric pressure. In some embodiments, the dried saponin product is kept in contact with the dry gas for at least 1 minute. For instance, the dried saponin product can be kept in contact with the dry gas for 5 minutes or longer.

If desired, following repeated dry gas exposure, vacuum pressure removal of dry can be repeated any number of times. In some embodiments, the step of contacting the dried saponin product with a dry gas followed by the step of vacuum pressure removal of dry gas is repeated seven times.

Optionally, the contacting of the dried saponin product with a dry gas followed by the vacuum pressure removal of dry gas can be at greater than 2° C. For instance, the contacting of the dried saponin product with a dry gas followed by the vacuum pressure removal of dry gas can be performed at greater than 34° C.

In some embodiments, an inert gas, in particular nitrogen, is used as a dry gas. However, any water-free, non-reactive (or weakly-reactive) gas can be used.

The method disclosed herein is suitable for producing purified saponins products containing, at least one partially purified Quillaja saponin selected from the group QS-7, QS-17, QS-18, and QS-21. Typically, purifications include at least QS-21. Optionally, however, purifications could include more than one kind of Quillaja saponin. Likewise, the purifications could include Quil-A. Similarly, the composition could also include a plurality of different saponins selected from different classifications (families) of organisms.

This disclosure also relates to the highly purified QS-21 produced according to the methods disclosed herein.

The disclosure further relates to use of the highly purified QS-21 saponin product produced by the disclosed method in an immunogenic composition. Typically, the immunogenic composition includes an antigenic epitope able to produce an immunogenic reaction to an antigen, e.g., from a pathogen and highly purified QS-21 saponins produced by the disclosed method. Optionally, the immunogenic composition can further includes one or more additional Quillaja saponins selected from the group QS-7, QS-17, QS-18, and QS-21. Similarly, the immunogenic composition can further include one or more different saponins selected from different classifications (families) of organisms. Optionally, the immunogenic composition also includes a second adjuvant. The adjuvant can be, for example, liposomes. Similarly, the adjuvant can be 3D-monophosphoryl lipid A (3D-MPL). Optionally, the immunogenic composition could include both liposomes and 3D-MPL.

The abbreviation 3D-MPL represents 3-O-deacylated monophosphoryl lipid A (also referred to as 3-de-O-acylated monophosphoryl lipid A, 3-O-desacyl-4'-monophosphoryl lipid A, 3D-monophosphoryl lipid A and 3D-MLA), a nontoxic derivative of lipopolysaccharide known to cause preferential induction of type 1 T-cells immune responses. Garcon et al. EP822831B2 and Moore, Vaccine. 1999; 17:2517-27. 3D-MPL is composed of 4'-monophosphoryl lipid A molecules in which position 3 of the reducing end glucosamine has been selectively de-acylated. 3D-MPL is described in GB 2 220 211 (Ribi) as a mixture of primarily 3 types of 3-de-O-acylated-4'-monophosphoryl lipid A with 4, 5 or 6 acylchains and is manufactured by Corixa dba GlaxoSmithKline. A form of 3D-MPL is disclosed in WO 92/116556.

Liposomes are artificially prepared vesicle made of lipid bilayer. QS-21 is capable of causing necrosis at the injection site but this can be avoided by use of formulations containing a combination of QS-21 and a sterol, Possible sterols for use include β-sitosterol, stigmasterol, ergosterol, ergocalciferol and cholesterol and the compositions of the invention are those forming a liposome structure. Generally such liposomes are composed of neutral lipids, for example phosphatidylcholine, which is preferably non-crystalline at room temperature, for example, egg yolk phosphatidylcholine, dioleoyl phosphatidylcholine, or dilauryl phosphatidylcholine. The liposomes can also contain a charged lipid as this will increase the stability of the liposome-saponin structure for liposomes composed of saturated lipids. Suggested formulations of saponins with lipids are described in WO 1996/033739(A1).

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solvent component concentrations, and reaction conditions such as temperatures, pressures and cycle times are intended to be approximate. Thus, where a concentration is indicated to be at least (for example) 22% volume/volume acetonitrile, it is intended that the concentration be understood to be at least approximately (or "about" or "~") 22% volume/volume acetonitrile. Likewise, the term "about" when used in reference to a stated percentage is used to indicate that the given value is approximate and may vary by plus or minus 5%.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., saponin, solvent, organic component) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of terms are provided. Additional terms and explanations can be provided in the context of this disclosure.

The verb "purify" (e.g., with respect to a saponin in a solution) means to separate a saponin in a solution from some other undesired components in the solution (e.g., solubilizing components). Purify is a relative term, and does not require that all traces of the other undesired components be removed from the composition. For instance, a saponin in a solution is considered purified by the method disclosed herein when at least 90% of solubilizing components from the solution have been separated from the saponin.

The term "at least one saponin in a first solvent" refers to a mixture that is dispersed at the molecular or micellar level of one or more substances (e.g., one or several saponins), in one or more other substances (e.g., solvent) which can (but need not necessarily) consist of primarily or exclusively of liquid phase components. The term "solvent," refers to a substance, liquid or miscible, partially miscible or immiscible mixture of two or more liquids, capable of completely or partially dispersing another substance, e.g., a saponin, into solution. A "solubilizing component" is a component whose molecules act to disperse other substances, such as saponins into solution.

The term "molecule" refers to either atoms of a single chemical elements, or of groupings of two or more atoms of the same or different chemical elements, connected by covalent bonds. An "organic molecule" refers to a molecule composed of at least one carbon atom. An "alcohol" is any organic molecule in which a hydroxyl functional group (oxygen and hydrogen, —OH) is bound to a carbon atom. This structure is usually covalently connected to other carbon or hydrogen atoms. The term acid means any chemical that is a proton donor (i.e., yields hydronium ions ($H_3O^+$) when dissolved in water). A "base" is any compound that is a proton acceptor (i.e., yields hydroxide ions ($OH^-$) when dissolved in water). The term acetonitrile refers to the compound having the structural formula $CH_3CN$. The measurement "volume/volume" (abbreviated as % vol/vol) is used to refer to the volume of a liquid in mL per 100 mL of the resulting solution.

The verb "replace" (with respect to replacing at least a portion of the solubilizing component with an exchange solvent) means to substitute at least one molecule of a solubilizing component of a first solvent with one or more different molecules. Not all molecules of the first solvent need to be substituted with different molecules for the solvent to be considered replaced. For example, replacement of greater than 40% of a solvent is sufficient to constitute replacement. For instance replacement of about 75% of a solvent is sufficient to constitute replacement.

The term "solubilizing component" means any molecule in a solution.

The verb "remove" (with respect to a solvent) means to dissipate by converting to vapor. Not all molecules of a solvent need to be absent for the solvent to be considered removed. For instance, solvent is considered to have been removed from saponins purified by the method disclosed herein when at least 90% of solvent components have been separated from the saponin. For example, separation of greater than 93% of solvent components is sufficient to constitute removal. For instance replacement of about 95% of solvent components is sufficient to constitute removal. Thus, the verb "remain" (with respect to solvent molecules in dried saponin products) refers specifically to solvent molecules (e.g., water and/or other solubilizing component molecules) that persist in a dried saponin product despite removal procedures that have been performed on the saponin product to dry it or otherwise rid it of solvent. In fact, because not infrequently some solvent particles often persist in a dried saponin product despite removal procedures one has performed to rid it of a substantial portion of solvent, to be considered "dried" a saponin product need not necessarily be entirely free of solvent molecules.

The term "gas-cleansed dried saponin product" refers to a saponin product that typically contains less than 50 ppm acetonitrile, less than 5% water by weight and less than 0.40% of the main degraded saponin byproduct. These saponins results from the process of contacting a dried saponin product with a dry gas to allow solvent molecules that remained bound within the saponin product after removal to disperse into the dry gas. As used herein, the term "dry gas" means any gas that is substantially or entirely free of water molecules. A dry gas can be composed of only one kind of gas molecules or a composite of two or more different types of gas molecules. The verb "disperse" (in regards to solvent molecules) means to diffuse, move away, scatter or to spread. Not all solvent molecules that remain within the saponin product after solvent removal must become unbound for dispersion, as defined herein, to have occurred. For example, diffusion of greater than 10% of remaining solvent molecules out of the dried saponin product into the dry gas is sufficient to constitute diffusion as defined herein. For instance diffusion of about 15% of remaining solvent molecules out of the dried saponin product into the dry gas is sufficient to constitute diffusion.

The term "semi-permeable containment vessel" refers to any structure able to receive some volume of a saponin in a solution, some part of which is permeable to solvent components but impermeable to one or more solutes (such as saponins) such that at least one saponin in will be retained by the containment vessel, and at least one solvent particle can exit the portion of the vessel that acts to retain the saponin. The terms "container" and "containment vessel" both represent structures able to hold a volume of a liquid. The term "non-permeable" as applied to a membrane or container, refers to a material that substantially blocks the passage of all solution components (such as both saponins, and solvent) across its surface. The term "entirely permeable" refers to a portion of a membrane, or substance, that is permeable to both solvent components and one or more solute components (such as saponins). A "channel" is an entirely permeable pathway through which both solvent components and solute components can travel. The verb "retained" (in regards to saponins that do not pass through the permeable portions of containment vessels) means to not travel across the semi-permeable membrane and leave the containment vessel.

The term "semi-permeable membrane" refers to a membrane, or substance, permeable to solvent components but impermeable to one or more solutes (such as saponins). The term "semi-permeable barrier" likewise refers to a membrane, or substance, permeable to solvent components but impermeable to one or more solutes (such as saponins). A semi-permeable membrane or barrier can facilitate passive diffusion of solvent particles into or out of a first solvent if placed between solvents of differing compositions by allow solvent components to move down their concentration gradients by crossing the membrane. Solvent particles can also be forced across semi-permeable membranes or barriers while solute partials are selectively retained within the membrane or barrier by applications of pressure greater than the pressure of the environment surrounding the semi-permeable membrane or barrier to solutions constrained by the membrane or applications of vacuum pressure to portions of the semi-permeable membrane or barrier opposite solutions constrained by the membrane or barrier.

The verb "immersed" (in relationship to immersing a semi-permeable containment vessel containing at least one saponin in first solvent into the exchange solvent) means that at least a portion of the semi-permeable containment vessel is simultaneously in contact with both a first and exchange solvent. It is not required that the entire semi-permeable containment vessel come in contact with one or both solvents for immersion to have occurred. Nor is it necessary for the entire semi-permeable portion of the containment vessel to be entirely in contact with one or both solvents for the vessel to be considered "immersed."

The verb "separated" (in reference to compartments of non-permeable container separated by a semi-permeable membrane) means that the semi-permeable membrane acts as an intervening barrier defining a first and second compartment of the non-permeable container. The semi-permeable membrane need not be composed entirely of semi-permeable material for it to be considered as "separating" the first and second compartment. For instance, some portion of the membrane can be non-permeable. Additionally, the first and second compartments of the non-permeable container can be individually defined solely by their being separated from other parts of the container by the semi-permeable membrane.

The term "equilibrium" (e.g., in relationship to a first solvent and an exchange solvent separated by a semi-permeable membrane allowed to reach equilibrium by diffusion) refers to when the concentrations of all solvent particles able to cross the semi-permeable membrane in two solvents separated by a semi-permeable membrane become equal in the first solvent and the exchange solvent. This equilibrium can occur passively due to solvent particles traveling down their concentration gradients. However, some form of agitation or pressure can also be employed to accelerate this process.

The term "vacuum" means a region having a reduced gas pressure as compared to local atmospheric pressure. As used herein, "vacuum" does not mean a space totally devoid of matter. The term "negative pressure" also refers to areas that have a lower pressure than the local atmospheric pressure in surrounding areas.

As used herein the term "atmospheric pressure" means the force exerted on the surface of a given unit of area by the weight of the air above that surface. The standard atmospheric pressure is about 1000 millibars. However, precise atmospheric pressure measurements are location and elevation specific and will vary between different places. Likewise, the atmospheric pressure at one location will also vary over time.

The measurement "parts per million" (abbreviated as "ppm") is used herein to express the concentration by volume or weight of a liquid or solid contaminant, respectively, per million parts of dried saponin product. The term "water by weight" as used herein in regards to a percentage values, refers to the percent of a dried saponin product's weight that is attributable to water.

An "immunogenic composition" is a composition of matter suitable for administration to a human or animal subject that is capable of eliciting a specific immune response, e.g., against a pathogen. As such, an immunogenic composition includes one or more antigens or antigenic epitopes. The term 'antigen' is well known to the skilled person. The antigen can be in the context of an isolated protein or peptide fragment of a protein, or can be a partially purified preparation derived from a pathogen. Alternatively, the antigen can be in the context of a whole live or inactivated pathogen. An antigen can be a protein, polysaccharide, peptide, nucleic acid, protein-polysaccharide conjugates, molecule or hapten that is capable of raising an immune response in a human or animal. Antigens may be derived, homologous or synthesised to mimic, molecules from viruses, bacteria, parasites, protozoan or fungus. The antigen may also be derived, homologous to, or synthesised to mimic, molecules from a tumour cell or neoplasia. In a further embodiment of the invention the antigen is derived, homologous to, or synthesised to mimic, molecules from a substance implicated in allergy, Alzheimer's disease, atherosclerosis, obesity and nicotine-dependence. Typically, when an immunogenic composition or vaccine includes a live pathogen, the pathogen is attenuated, that is, incapable of causing disease in an immunologically competent subject. In other cases, an immunogenic composition or vaccine includes a whole inactivated (or killed) pathogen. The inactivated pathogen can be either a wild-type pathogenic organism that would otherwise (if not inactivated) cause disease in at least a portion of immunologically competent subjects, or an attenuated or mutant strain or isolate of the pathogen.

Saponins

Current methods of QS-21 purification typically involve two consecutive lyophilization cycles to dry the product and remove residual acetonitrile to an acceptable degree. These current methods are not optimal because, in addition to taking 14 days to return a purified QS-21 product, QS-21 dry powder produced by these methods is heterogeneous in consistency. After the first lyophilization, the preliminarily dried saponin product is resuspended in water for the second lyophilization step. This results in heterogeneity of the final saponin product because the preliminarily dried saponin product rarely can be completely dissolved. Homogeneity of the final product is an indicator of highly uniform product purity.

The method disclosed herein enables the production of purified QS-21 in less than half-the amount of time of current methods. Moreover, as shown in Table 1 below, saponins purified by this method retain no more solvent and water than purified saponin products obtained using current procedures, typically involving multiple lyophilization steps which can take twice as long. Furthermore, the gas-cleansed dried saponin product produced by the disclosed method is more homogenous than dried saponin products produced by current methods.

Saponins are surface-active glycosides, usually of plant origin, and more rarely, other organisms such as starfish or sea cucumbers. Saponins are composed of a hydrophilic region (usually composed of one or more sugar chains) in association with a hydrophobic region (usually composed of either a steroid or a triterpenoid structure). Saponins frequently possess hemolytic activity, immune adjuvant activity, the ability to complex with cholesterol, and, in some instances, antibiotic activity. Saponins are also typified by an ability to generate soap-like foam when they are shaken in water solutions. Saponins are well known.

TABLE 1

Residual acetonitrile (in ppm) and residual water (in % moisture) in a purified QS-21 saponin product produced by the disclosed method.

| Run Number | Sample Number | Sample collection | Moisture (%) | ACN (ppm) | QS-21 (%) |
|---|---|---|---|---|---|
| 1 | A | After lyophilization cycle | 1.5 | 19 | 98.27 |
|  |  | After pulse | 1.3 | 5 | 98.22 |
|  | B | After lyophilization cycle | 1.6 | 16 | 98.24 |
|  |  | After pulse | 1.3 | 3 | 98.25 |
| 2 | A | After lyophilization cycle | 1.0 | 44 | 98.19 |
|  |  | After pulse | 1.5 | 23 | 98.13 |
|  |  | Powder dispensed to final container | 1.3 | 4 | 98.17 |
|  | B | After lyophilization cycle | 1.1 | 28 | 98.16 |
|  |  | After pulse | 1.5 | 13 | 98.19 |
|  |  | Powder dispensed to final container | 1.7 | 8 | 98.24 |

Exemplary triterpene glycosides saponins constitute up to 10% of the bark of the South America tree *Quillaja saponaria* Molina. The immunostimulatory action of these saponins has been evaluated for more than 50 years. There are estimated to be close to 50 unique saponins from *Quillaja Saponaria* (referred to herein as "Quillaja saponins "). Most have the same triterpene base, quillaic acid, and are acetylated 3,28 bisdesmonosides (with oligosaccharide linked to the 3-and 28-carbons of quillaic acid). Difference between unique Quillaja saponins are primarily found in the glycocilataion pattern or acetylation pattern. To date, twenty two Quillaja saponins have been isolated and extensively characterized. Six of these, QS-7, QS-17, QS-19, QS-18 and QS-21 show significant adjuvant activity in mice and other mammals. However, these saponins vary widely in their toxicity, with QS-18 and QS-19 being more toxic at lower doses than other Quillaja saponins and QS-21 showing low toxicity but strong adjuvant activity. QS-7 also has immune modulating properties and very low toxicity but requires higher doses for adjuvant activity. For a review of the different adjuvant properties of Quillaja saponins see Kensil CR, et al., Separation and characterization of saponins with adjuvant activity from *Quillaja saponaria* Molina cortex. *J Immunol.* 146(2):431-7 (1991).

Quillaja saponins have been shown to induce strong type Th1 and Th2-type immune response to antigens as well as moderate cytotoxic T lymphocytes (CTL) responses to some proteins. Kensil CR. Saponins as vaccine adjuvants. *Crit Rev Ther Drug Carrier Syst.* 13:1-55 (1996). Consequently, Quillaja saponins can be used as adjuvants in wide range of immunogenic compositions. For example, Quillajasaponins can be used to induce Th1 responses against intracellular pathogens and malignant cells as well as suppress IgE-mediated allergic responses. However, since unpurified quillaja extract is composed of a heterogeneous mix of saponins with significant differences in their toxicity, separation of non-toxic Quillaja saponins from the other more toxic saponins is required for their safe immunological use.

Early attempts to purify Quillaja saponin adjuvants are described in Dalsgaard, Archiv fuer die gesamte Virusforschung 44:243 (1974). Dalsgaard's preparation, aqueous extract of Quillaja saponins partially purified by anion exchange and gel filtration is now commercially available under the name "Quil-A" and has been used in veterinary vaccines since the early 1970s. While partially purified, the saponins of Quil A are considerably heterogeneous, showing some 20-25 reverse phase chromatography peaks. A more recent Quil A formulation called Iscoprep 703 is further purified to consist only of 10 reverse phase chromatography peaks with the most toxic components excluded.

In one particular embodiment, the procedure disclosed here can be used for the purification of Quillaja saponin QS-21. QS-21 constitutes an HPLC purified fraction from the *Quillaja Saponaria* Molina tree bark and a method for its isolation is disclosed in U.S. Pat. No. 5,057,540. *Quillaja* saponin QS-21 has particularly low toxicity but induces strong Th1 and Th2-type immune response to antigens as well as moderate CTL responses to some proteins.

Obtaining a Saponin in a First Solvent

It should also be understood that it is well known to those skilled in the art of saponin purification, that other chromatographic procedures can be used to purify any other *Quillaja saponaria* Molina saponins, as well as saponins from other organisms, and that these purifications processes can be also altered to obtain mixtures of more than one kind of saponin in a solvent (as in Cox et al. U.S. Pat. No. 6,352,697 and Kensil et al. '540).

Typically it is desirable, in purifying *Quillaja*saponins, to use acetonitrile and water in the purification procedure, however, a multitude of other solvents can be used for the extraction of Quillaja saponins, and other plant species' saponins, from plant material. For instance, it is well known to those skilled in the art of saponin purification, that one can use a large number of organic solvents (e.g., acetonitrile, methanol, chloroform and alcohols, just to name a few), water, and many acids and bases for extraction of saponins from plant materials as well as compositions of organic solvents with acids and/or water for the purification of saponins. (See Kensll et al. '540 use of methanol and a methanol and acetic acid compositions, Cox et al. '697 use of an acetonitrile and acidic water composition, Kensll et al WO 98/24319 use of a chloroform, methanol, water and acetic acid mixture). A concentration of greater than 40% acetonitrile is optimal for elution of QS-21 off of a C8 HPLC column. Acetonitrile is a convenient solvent for use in the present method. However, any of the aforementioned compositions capable of bringing saponins into solution and/or separating saponins from other plant material can be used. Likewise, the precise percentage of acetonitrile used in the Examples is noted solely because it is optimal for C8 column extraction. One skilled in the art of saponin purification, would likewise know that a variety of concentrations of acetonitrile, or any solvent used, can vary depending on purification system employed.

Solvent Replacement

Once a saponin in a solvent has been obtained and purified to a degree appropriate for the intended use of the saponin, it is may be necessary, depending on the freezing properties of the solvent, to replace the solvent that the saponins with a different solvent to obtain a homogenous lyophilization product. A saponin's solubility in solvent changes as temperature decreases, therefore the homogeneity of a lyophilization product often requires lower solvent concentrations than those that must be used to bring them into solution or elute them off of chromatographic columns. Furthermore, some solvents which are miscible with water at room temperature separate into water-rich and solvent-rich domains during freezing. For instance, this effect is observed with aqueous solutions of acetonitrile, so it is necessary to reduce the level of acetonitrile to less than 20% to obtain homogeneous saponin product on freezing (see Zarzycki P K et al, Analyt Sci 22, 453-456[2006]). Elutions off of reverse phase chromatographic columns often require acetonitrile concentrations from about 30% to about 60%. Therefore, the proceeding purification procedures can result in a concentration of solvent above that favorable to obtain a homogenous lyophilization product.

There are a number of ways in which solvent replacement can be performed on a saponin in a solvent. For instance, diafiltration, as detailed above can be used. Ultrafiltration followed by dilution of retained buffer is also a suitable means of buffer replacement. Dialysis, is also another possible method that can be used to replace a solvent. As diafiltration allows for much higher volumes of solvent to be exchanged much faster than dialysis however, diafiltration can be used for performing solvent exchange on large-scale purifications.

An example of a solvent replacement method for a saponin in organic solvent solution is also described in detail in Examples hereinafter. Optimally, when the method disclosed herein is being performed on saponin samples in solutions of acetonitrile and one intends to further purify the sample by lyophilization, the final concentration of organic solvent after solvent replacement is less than about 22% volume-to-volume (vol/vol) acetonitrile. In certain embodiments the solution would consisting of less than 20% vol/vol acetonitrile. In one embodiment, a final concentration of about 18% vol/vol acetonitrile is obtained because, a concentration of acetonitrile lower than 20% is required to obtain homogeneous product on freezing (Zarzycki P K et al.). Thus, an 18% vol/vol acetonitrile is a convenient concentration to achieve by solvent replacement. However, for example, any acetonitrile concentration less than 22% can be used.

The solvent replacement procedure described in Examples is included by way of example only, and that there are several procedures functionally similar or equivalent to the diafiltration procedure detailed in Examples is well known to those skilled in the art of saponin purification. Such methods include, but are not limited to, dialysis and ultrafiltration followed by dilution. Diafiltration is exemplified herein because it allows large-scale production of saponins in replaced solvent and because the concentration of the retained species can be easily controlled during the continuous flow method of diafiltration, providing a gentle and reproducible solvent replacement method. Thus, diafiltration is a convenient solvent replacement method to use to achieve by solvent replacement. However, as noted, other similar processes such as ultrafiltration/dilution and dialysis can be used.

Solvent Removal

Following solvent replacement the solvent can be removed from the saponin product yielding a dried saponin product. Removal of solvent from saponins following chromatographic procedures can be accomplished by lyophilization. Lyophilization is performed on a solvent/solute mixture under a vacuum resulting in the sublimation of the solvent, and leaving behind the dried solute(s). Any pressure less than 100 microbar is likely to be suitable. Typically a vacuum of at least about 500 mBar is sufficient to promote efficient sublimation of a solvent. Although the pressure can be further reduced, doing so has little effect on drying rate, and under very low pressure conditions, efficiency of sublimation is decreased.

Although solvent removal can be performed simply by placing a liquid sample into a vacuum chamber, due to foaming as indicated above, product loss as well as decreases in product homogeneity can result from use of such a procedure. To prevent frothing, a saponin in a solvent can first be frozen and solvent can then be removed by sublimation under vacuum, a process called lyophilization or freeze drying. Generally, a relatively slow cooling rate of between 0.1° C. and 1.0° C./minute is used to promote development of large ice crystals that are conducive to vapor migration.

Additionally, one convenient method for lyophilization of saponin solutions is to use a Gore brand disposable LYOGUARD™ tray. These single-use, autoclavable lyophilization trays, comprise a chemically inert tray covered with a semi-permeable membrane that allows vapor but not liquid to pass, and therefore protect the product from external contamination during use. LYOGUARD™ trays are suitable for large-scale freeze-drying applications of saponins.

An example of a lyophilization procedure that can be performed on a saponin in replaced solvent is described in detail in Examples hereinafter. The procedure described in Examples is included by way of example only, any of the aforementioned procedures functionally similar or equivalent to the lyophilization procedure detailed in Examples well known to those skilled in the art of saponin purification, such as, controlled heat exposure and rotary evaporation can be used in place of the lyophilization to achieve similar or equivalent results.

For instance, it is well known to those skilled in the art of saponin purification that heat evaporation can be used to remove solvent particles from non-volatile solutes, such as saponins, where heat above the boiling point of the liquid solvent components is applied to a solution. Likewise, solvent evaporation in the form of rotary evaporation is well known to those skilled in the art of saponin purification.

Rotary evaporation involves solvent evaporation from solutes by placing the solvent solute mixtures in a vessel which is then rotated over heat while simultaneously being maintained under a vacuum though a tube that also acts as a condenser. The vaporized solvent exits the flask via the connecting tube and is collected as it recondenses in the condenser section. All non-volatile solute particles remain in the flask. Although rotary evaporation is commonly used to recovery non-volatile solutes eluted after chromatographic separation, this method is likely to not be optimal for saponin purifications because of the proclivity of saponins to produce foam when being mixed or undergoing temperature and pressure changes. Therefore, rotary evaporation can lead to product loss via the vacuum/condenser line. Controlled heat exposure can also produce sub-optimal results for evaporation of solvents from saponins because heating the sample can result in significant product degradation. Furthermore, any procedure that increases the length of time it takes for saponins to be purified increases the proportion of degraded saponin byproducts that can build up in the sample.

Gas Cleanse

Optionally, following solvent removal from the saponin in replaced solvent the dried saponin product can be further rid of solvent molecules by exposure to a dry gas followed by vacuum cycles yielding a gas-cleansed dried saponin (herein after this procedure is termed the "gas cleanse"). This procedure acts to desorb any loosely bound solvent partials from the dried saponin product. While most solvent removal procedures such a lyophilization, rotary evaporation, and heat exposure can be employed to remove a substantial portion of solvent particles from solutions comprising saponins in a solvent, not infrequently, some solvent particles will persist or remain stuck within to the final product. This is particularly likely to occur where the solubilizing component used is heavier than other solvent components as these will diffuse from the dried saponin product more slowly than other, lighter, solvent components. A gas cleanse allows these trapped particles to disperse away from and out of the dried saponin product.

Typically, although not necessarily, dried saponin product will be transferred to a clean vacuum chamber at the start of the pulse cycle. The dried saponin product is then exposed to a cycle consisting of changing the chamber conditions from vacuum to nitrogen rich conditions. Optionally, a dried saponin product can be exposed to greater that one such cycle. For instance, anywhere from one to ten such cycles can be used. Optionally however, greater than ten pulse cycles can be used. Although, typically, between four and eight such cycles are performed. For example, in one embodiment, seven such cycles are performed. Optionally, this cycling can be performed at a shelf temperature of greater than 20 degree Celsius. For example, a shelf temperature of greater than 30 degrees Celsius can be used. In some embodiments this cycling is performed at 34 degrees Celsius.

Initially the dried saponin product in a clean vacuum is exposed to vacuum conditions such as a pressure of about 50 microbar. Although the pressure can be further reduced, doing so has little effect on the efficacy of the gas cleanse. Likewise, any pressure less than 100 microbar is suitable. Once the desired pressure set-point is reached, the vacuum should be held for at least 20 minutes. Typically the vacuum pressure will be held for about 30 min. Following, application of the vacuum pressure, the vacuum pressure in the chamber is released with a dry gas such as nitrogen instead of ambient air. This prevents any further absorption in the sample of water from the air in the form of humidity. As well an entirely dry gas will have more free space in which particle desorption from the sample can occur. Dry gas should be entered into the system until a pressure of greater than 700 microbar is reached. Typically a pressure of about 800 microbar is used. However any pressure above atmospheric pressure is suitable. These conditions are held for about 5 minutes. This represents a pulse cycle. Typically, seven of these pulse cycles are performed in one lot, followed by the product discharge.

An exemplary pulse cycle procedure is also described and detailed in Examples hereinafter. It should be understood that procedure described in Examples is included by way of example only, and that any water-free gas or any combination of two or more water-free gases could likely be used in place of nitrogen. It should also be understood that some variations in other noted procedure parameters, such as the temperature, pressure, as well length of gas and vacuum exposure, could nonetheless generate gas-dried saponin products of identical or similar quality.

Purified Qs-21 Produced by the Disclosed Methods

This disclosure also relates to the highly purified QS-21 produced according to the methods disclosed herein. Quillaja saponin, QS-21 purified by these methods is more homogenous than that produced by other methods because the reduction of the number of required lyophilization to one. Moreover, despite only requiring one lyophilization and half the time of current methods of QS-21 purification, QS-21 purified by the current methods can contain lower than 50 ppm acetonitrile and less than 2% water by weight. Therefore the current method allows for production of a purified QS-21 product that is more homogeneous an comprises less residual solvent than purified QS-21 obtainable from existing methods in less time than existing methods require.

Furthermore, given QS-21's great pharmacological value arising from its low toxicity and ability to induce strong Th1 and Th2-type immune response to antigens as well as moderate cytotoxic T lymphocytes (CTL) responses to some proteins, the current disclosure also relates to the use of the highly purified QS-21 saponins obtained by the disclosed methods as an adjuvant in immunogenic compositions. Moreover, because potential necrosis that can be caused by QS-21 at injection site when QS-21 is used as an adjuvant can be avoided by use of formulations containing cholesterol. The current disclosure further relates to the use of QS-21 purified by the disclosed methods in combination with cholesterol, others lipids and/or 3D-MPL.

EXAMPLES

Purification of Saponin Qs-21 from Plant Material:

A solution of purified QS-21 in a solvent comprising acetonitrile can be prepared from an aqueous extract of *Quillaja saponaria* using methods well known in the prior art (e.g. U.S. Pat. No. 6,231,858 or U.S. Pat. No. 6,524,584).

Solvent Exchange

Following purification from plant material, solvent exchange was performed. The QS-21 solution at a concentration >20 g/L QS-21 and in a solvent mixture consisting of 60% volume/volume acetonitrile, 40% water, was diafiltered using a ultrafiltration unit (transmembrane pressure of approximately 2.5 bar, room temperature) through a 1,000 Dalton molecular weight cutoff membrane, against 4 volumes of a solvent consisting of approximately 18% volume/volume acetonitrile and 82% water. (1000 Da regenerated cellulose, from Millipore Pellicon 2 P2PLA was used here). The retentate was then collected, analyzed for QS-21 content by reverse phase HPLC analysis, and was diluted to a final QS-21 concentration of approximately 18 grams per liter by adding a solvent consisting of approximately 18% volume/volume acetonitrile and 82% water.

Solvent Removal

Following solvent exchange, solvent removal was performed. The QS-21 solution was lyophilized by freezing the lyophilization shelf to −56° C., performing a primary drying at a shelf temperature of −45° C. and 570 μbar for 15 hours, and a second primary drying segment at a shelf temperature of −15° C. and 200 μbar for 64 hours. This was followed by a secondary drying step at a shelf temperature of 34° C. and 200 μbar for 10 hours, a subsequent secondary drying segment at a shelf temperature of 34° C. and 100 μbar for 12 hours and a third secondary drying segment at a shelf temperature of 34° C. and 50 μbar for 12 hours.

Pulse Cycle

Following solvent evaporation the pulse cycle was performed. The lyophilized QS-21 was transferred to a clean vacuum chamber, and a cycle consisting of changing the chamber conditions from vacuum (30 min, 50 μbar) to nitrogen rich conditions (5 min, 800 mbar) was then performed 7 times at a shelf temperature of 34° C. to desorb any loose acetonitrile out of the lyophilized QS-21.

Following the techniques described above in Examples according to the disclosed methods, a gas-cleansed dried saponin product was produced.

Table 1, above, represents residual water and acetonitrile content in a saponin product produced b the disclosed methods (Run Number 1, Sample A and B). The amount of residual acetonitrile in the sample was determined by HPLC. The amount of residual water in the sample was determined by Karl Fisher determination. Both samples examined contained less than 50 ppm acetonitrile and less than 2% residual water content.

We claim:

1. A method for purifying at least one saponin in a solution comprising the steps of:
    a) providing at least one saponin in a first solvent comprising a solubilizing component;
    b) replacing at least a portion of the solubilizing component with an exchange solvent, thereby producing a replaced solvent; and
    c) removing the replaced solvent, to produce a dried saponin product comprising at least one saponin, wherein the first solvent comprises at least partially purified QS-21; and the first solvent comprises at least 22% volume/volume acetonitrile; and the replaced solvent comprises no more than 21% volume/volume acetonitrile.

2. The method of claim 1, wherein the solubilizing component of step (a) completely or partially disperses the at least one saponin into the solvent.

3. The method of claim 1, wherein the first solvent comprises an HPLC column eluate.

4. The method of claim 1, wherein the first solvent comprises a C8 HPLC column eluate.

5. The method of claim 1, wherein the first solvent comprises a phenyl chromatography column eluate.

6. The method of claim 1, wherein the first solvent comprises at least about 50% volume/volume acetonitrile.

7. The method of claim 1, wherein the first solvent comprises between about 30% and 65% volume/volume acetonitrile.

8. The method of claim 1, wherein the first solvent comprises between about 40% and 62% volume/volume acetonitrile.

9. The method of claim 1, wherein the first solvent comprises between about 58% and 62% volume/volume acetonitrile.

10. The method of claim 1, wherein replacing the solubilizing component is by one or more of: diafiltration, ultrafiltration or dialysis.

11. The method of claim 1, wherein exchanging the at least a portion of the solubilizing component is by exchanging an identical volume of the first solvent with an exchange solvent.

12. The method of claim 1, wherein replacing the at least a portion of the solubilizing component is by exchanging a non-identical volume of the first solvent with an exchange solvent.

13. The method of claim 1, wherein the replaced solvent comprises at least 15% volume/volume acetonitrile.

14. The method of claim 1, wherein the replaced solvent comprises between 15% and 21% volume/volume acetonitrile.

15. The method of claim 1, wherein replacing the at least a portion of the solubilizing component is done in a system comprising a semi-permeable containment vessel.

16. The method of claim 15, wherein the semi-permeable containment vessel is selectively permeable such that when the at least one solvent component will pass through the permeable portion of the vessel and at least one saponin will be retained.

17. The method of claim 15, wherein the semi-permeable containment vessel comprises a single semi-permeable membrane.

18. The method of claim 17, wherein solvent replacement is achieved by immersing the semi-permeable containment vessel comprising the at least one saponin and a first solvent in an exchange solvent and allowing the solvents separated by the membrane to reach equilibrium by diffusion.

19. The method of claim 15, wherein the semi-permeable containment vessel comprises a channel that is surrounded by a semi-permeable structure.

20. The method of claim 19, wherein the channel is entirely permeable to the solution including the at least one saponin in a solvent.

21. The method of claim 19, wherein the channel constitutes the inside of the containment vessel, and any portion of the semi-permeable structure not in contact with the channel constitutes the outside of the containment vessel.

22. The method of claim 21 comprising moving the at least one saponin and a first solvent through the channel of the containment vessel at a positive pressure relative to the outside of the vessel such that at least one component of the solution is forced across the semi-permeable portion of the containment vessel.

23. The method of claim 22, wherein replacing at least a portion of the solubilizing component with an exchange solvent is done by adding the exchange solvent to the inside of the containment vessel.

24. The method of claim 15, wherein the semi-permeable containment vessel comprises a non-permeable container comprising a first compartment and a second compartment separated by a semi-permeable membrane.

25. The method of claim 24, further comprising placing the at least one saponin and a first solvent into the first compartment of the containment vessel.

26. The method of claim 25 further comprising making the first compartment of the containment vessel a positive pressure relative to the second compartment such that at least one component of the solution is forced across the semi-permeable portion of the containment vessel.

27. The method of claim 26 further comprising replacing at least a portion of the solubilizing component with an exchange solvent by adding exchange solvent to the first compartment of the vessel.

28. The method of claim 1, further comprising removing the replaced solvent by one or more of: lyophilization, heat exposure or rotary evaporation.

29. The method of claim 1, further comprising repeating the removal step at least once.

* * * * *